(12) United States Patent
Naoe et al.

(10) Patent No.: US 8,673,888 B2
(45) Date of Patent: *Mar. 18, 2014

(54) DEPSIPEPTIDE FOR THERAPY OF KIDNEY CANCER

(75) Inventors: Yoshinori Naoe, Yokohama (JP); Susan E. Bates, Bethesda, MD (US)

(73) Assignees: The United States of America, represented by the Secretary, Department of Health and Human Services, Washington, DC (US); Astellas Pharma Inc., Tokyo (JP)

( * ) Notice: Subject to any disclaimer, the term of this patent is extended or adjusted under 35 U.S.C. 154(b) by 1009 days.

This patent is subject to a terminal disclaimer.

(21) Appl. No.: 10/508,958

(22) PCT Filed: Mar. 27, 2003

(86) PCT No.: PCT/JP03/03823
§ 371 (c)(1),
(2), (4) Date: Dec. 12, 2005

(87) PCT Pub. No.: WO03/084611
PCT Pub. Date: Oct. 16, 2003

(65) Prior Publication Data
US 2006/0135413 A1 Jun. 22, 2006

Related U.S. Application Data

(60) Provisional application No. 60/369,868, filed on Apr. 5, 2002.

(51) Int. Cl.
*A01N 43/00* (2006.01)
*A61K 31/33* (2006.01)
*A01N 31/00* (2006.01)
*A61K 31/10* (2006.01)

(52) U.S. Cl.
USPC .......................................... 514/183; 514/713

(58) Field of Classification Search
USPC ................................. 514/183, 713
See application file for complete search history.

(56) References Cited

U.S. PATENT DOCUMENTS

| | | | |
|---|---|---|---|
| 4,977,138 | A | 12/1990 | Okuhara et al. |
| 7,056,883 | B2 | 6/2006 | Ito et al. |
| 7,056,884 | B2 | 6/2006 | Nakajima et al. |
| 2002/0065282 | A1* | 5/2002 | Georges et al. ............ 514/238.2 |
| 2005/0070467 | A1 | 3/2005 | Naoe et al. |
| 2005/0187149 | A1 | 8/2005 | Naoe et al. |
| 2005/0191713 | A1 | 9/2005 | Sasakawa et al. |
| 2006/0223747 | A1 | 10/2006 | Ito et al. |

FOREIGN PATENT DOCUMENTS

| | | |
|---|---|---|
| JP | 7-64872 | 7/1995 |
| WO | 02/085400 | 10/2002 |
| WO | 03/017763 | 3/2003 |

OTHER PUBLICATIONS

Ueda, H.; Nakajima, H.; Hori, Y.; Fujita, T.; Nishimura, M.; Goto, T.; Okuhara, M. "FR90128, A novel antitumor bicyclic depsipeptide produced by *Chromobacterium violaceum* No. 968 I. Taxomony, fermentation, isolation, physico-chemical and biological properties, and antitumor activity", Mar. 1994, The Journal of Antibiotics, vol. 47(3); pp. 301-310.*
Kitazono Masaki, et al., : "The histone deacetylase Inhibitor FR901228 preferentially enhances adenovirus transgene expression in malignant cells", Proceedings of the American Association for Cancer Research Annual, vol. 43, p. 799, 2002 (English abstract only).
Masaki Kitazono, et al., : "Enhanced adenovirus transgene expression in malignant cells treated with the histone deacetylase Inhibitor FR901228", Cancer Research, vol. 61, pp. 6328-6330 Sep. 1, 2001.
Masaki Kitazono, et al., : "Adenovirus HSV-TK construct with thyroid-specific promoter: enhancement of activity and specificity with histone deacetylase inhibitors and agents modulating the camp pathway", International Journal of Cancer, vol. 99, pp. 453-459 2002.
Victoria M. Richon, et al., : "Histone deacetylase inhibitors: a new class of potential therapeutic agents for cancer treatment", Clinical Cancer Research, vol. 8, No. 3, pp. 662-664, 2002.
Hidenori Nakajima, et al., : "FR901228, a potent antitumor antibiotic, is a novel histone deacetylase inhibitor", Experimental Cell Research, vol. 241, pp. 126-133 1998.
Michael S. Finnin, et al., : "Structures of a histone deacetylase homologue bound to the TSA and SAHA Inhibitors", Nature, vol. 401, pp. 188-193 Sep. 9, 1999.
Khan W. Li, et al., : "Total synthesis of the antitumor depsipeptide FR-901228", J. Am. Chem.Soc., vol. 118, No. 30, pp. 7237-7238 1996.
Victor Sandor, et al., : "Phase I trial of the histone deacetylase inhibitor, depsipeptide (FR901228, NSC 630176), in patients with refractory neoplasma", Clinical Cancer Research, vol. 8, pp. 718-728 2002.

(Continued)

*Primary Examiner* — Kendra D Carter
(74) *Attorney, Agent, or Firm* — Oblon, Spivak, McClelland, Maier & Neustadt, L.L.P.

(57) ABSTRACT

The present invention provides a therapeutic agent of kidney cancer, which comprises FK228 of the formula (I) or a salt thereof. FK228 or a salt thereof, which is an active ingredient in the present invention, shows a superior antitumor activity in vivo against kidney cancer.

6 Claims, 1 Drawing Sheet

(56) References Cited

OTHER PUBLICATIONS

Abstract of: Inoue, K., et al., "Subrenal Capsule Assay-An Experimental Study and Clinical Application to Chemosensitivity Tests," Gan to Kagaku Ryoho, May 1987, 14 (5 Pt2): 1629-1635.

Bogden, A. E., et al., "Growth of Human Tumor Xenografts Implanted Under the Renal Capsule of Normal Immunocompetent Mice," Expl Cell Biol., 47, 1979, pp. 281-293.

Nishimura, M., et al., "A New Antitumor Antibiotic, FR900840, III. Antitumor Activity Against Experimental Tumors," The Journal of Antibiotics, vol. XLII, No. 4, Apr. 1989, pp. 553-557.

Marks, P. A., et al., "Histone Deacetylase Inhibitors: Inducers to Differentiation or Apoptosis of Transformed Cells," Journal of National Cancer Institute, vol. 92, No. 15, Aug. 2, 2000, pp. 1210-1216.

Hirotsugu Ueda, et al., "Antitumor Activities on Experimental Tumors in Mice", The Journal of Antibiotics, vol. 47, No. 3, Mar. 1994, pp. 315-323.

Proceedings of the Japanese Cancer Association, 2001, vol. 60, p. 597 (w/English Translation).

Hirotsugu Ueda, et al., "Antitumor Activities on Experimental Tumors in Mice", The Journal of Antibiotics, vol. 47, No. 3, Sep. 20, 1993, pp. 315-323.

U.S. Appl. No. 13/046,082, filed Mar. 11, 2011, Naoe, et al.

Data against kindey cancer with a date-stamp of Apr. 11, 2001. The data is no longer available from the website. The data availabe from the web-site is that as of Sep. 2003. The URL is as follows: http://dtp.nci.nih.gov/dtpstandard/servlet/dwindex?searchtype=NSC&chemnameboolean=and&outpufformat=html&searchlist=630176&tSubmit=Submit.

* cited by examiner

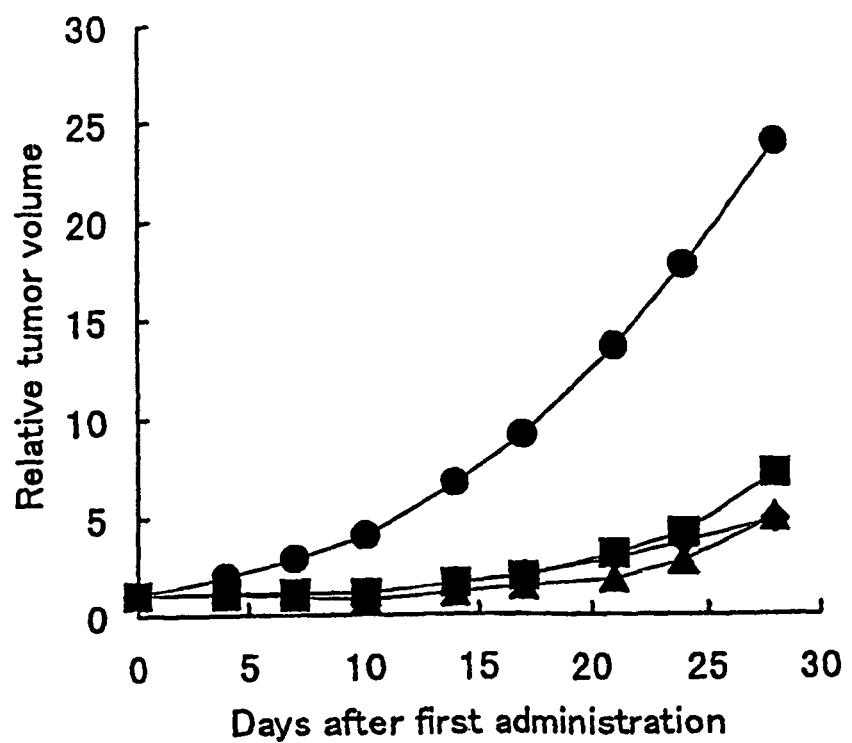

DEPSIPEPTIDE FOR THERAPY OF KIDNEY CANCER

TECHNICAL FIELD

The present invention relates to a method of treating kidney cancer and a therapeutic agent of Kidney cancer.

BACKGROUND ART

It has been pointed out that substances and compounds reported to have an antitumor activity based only on in vitro data alone generally do not allow anticipation of their effects in the in vivo results. In other words, a substance showing an antitumor activity in vitro does not necessarily show an antitumor activity also in vivo, and therefore, the application of a substance showing an antitumor activity in vitro directly as an anti-cancer agent is problematic.

For example, it has been reported that a compound (Sequence Listing SEQ ID NO. 1) of the formula (I)

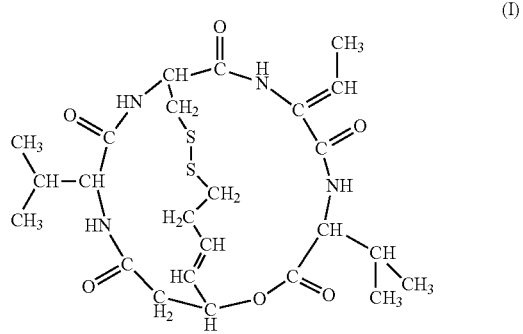 [SMILES: C/C=C1\NC(=O)C2CSSCC/C=C/C(CC(=O)NC(C(C)C)C(=O)N2)OC(=O)C(C(C)C)NC1=O]

induces a strong antitumor activity by selectively inhibiting histone deacetylase. It has been also reported that this substance causes high acetylation of histone in the cells treated with this substance, and as a result, induces a transcription controlling activity of various genes, a cell cycle inhibitory activity and an apoptosis inhibitory activity (JP-B-7-64872, H. Nakajima et al., Exp. Cell Res. 241, 126-133 (1998)). As the situation stands, however, there are many problems yet to be solved, such as effectiveness of in vitro results in in vivo application, in vivo effectiveness against any tumor and the like. The antitumor activity in vitro against kidney cancer has been reported, but an antitumor activity in vivo against kidney cancer has not been reported.

Histone deacetylase is a metallo deacetylase having Zn coordinated at the active center (M. S. Finnin et al., Nature, 401, 188-193 (1999)). This enzyme is considered to change affinity of various acetylated histones for DNA. The direct biological phenomenon provided thereby is a change in the chromatin structure. The minimum unit of the chromatin structure is a nucleosome wherein a 146 bp DNA winds around a histone octamer (H2A, $H_2B$, H3 and H4, 2 molecules each, core histone) 1.8 times counterclockwise. The core histone stabilizes the nucleosome structure as the positive charge of the N-terminal of each histone protein interacts with DNA. The acetylation of histone is controlled by the equilibrium relationship between acetylation reaction, in which histone acetyltransferase is involved, and the deacetylation reaction, in which histone deacetylase is involved. The acetylation of histone occurs in an evolutionarily well-conserved lysin residue in the N-terminal of a histone protein, whereby, it is considered, the core histone protein loses the charge of the N-terminal, the interaction with DNA decreases, and the structure of nucleosome is instabilized. Conversely, therefore, deacetylation of histone is considered to stabilize the nucleosome structure. However, the degree of changes in the chromatin structure caused by the acetylation is unclear nor is it clear how it is related to the secondarily induced control of transcription.

DISCLOSURE OF THE INVENTION

The present inventors have conducted intensive studies in an attempt to solve the above-mentioned problems, and found a therapeutic agent for kidney cancer, which is capable of confirming its antitumor effect in vivo, particularly in human patients with kidney cancer, which resulted in the completion of the present invention.

Accordingly, the present invention provides the following.

(1) A method of treating kidney cancer in mammals, which comprises administering an effective amount of a compound of the formula (I)

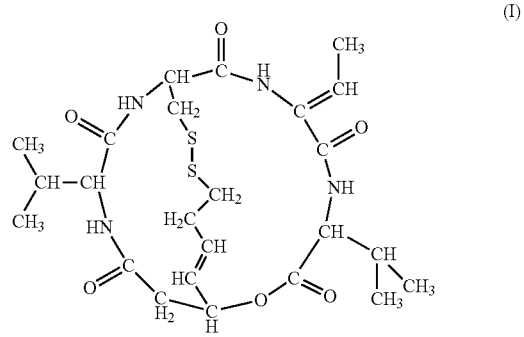 [SMILES: C/C=C1\NC(=O)C2CSSCC/C=C/C(CC(=O)NC(C(C)C)C(=O)N2)OC(=O)C(C(C)C)NC1=O]

or a salt thereof to a mammal.

(2) The treatment method of kidney cancer according to the above-mentioned (1), wherein the compound of the formula (I) is a compound of the formula (II)

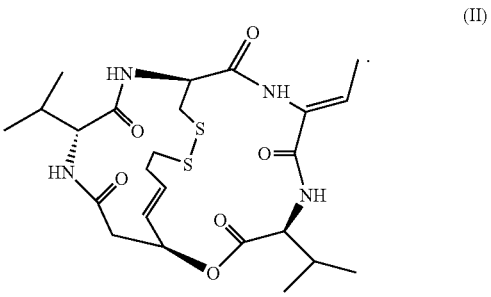 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

(3) The treatment method of kidney cancer according to the above-mentioned (1), wherein the mammal is a human.

(4) A method of suppressing growth of a cancerous tumor of the kidney in mammals, which comprises administering an effective amount of a compound of the formula (I)

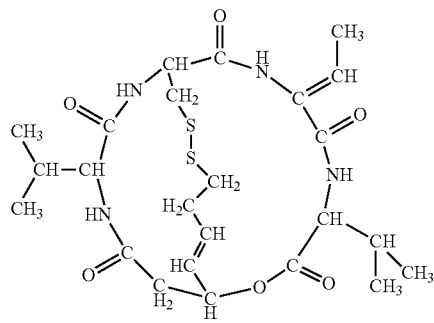
(I)

or a salt thereof to a mammal.

(5) The method of suppressing growth of the cancerous tumor of the kidney according to the above-mentioned (4), wherein the compound of the formula (I) is a compound of the formula (II)

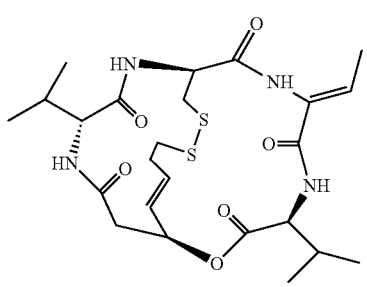
(II)

(6) The method of the above-mentioned (4) for suppressing the growth of the cancerous tumor of the kidney in vivo.
(7) The method of the above-mentioned (6), wherein the in vivo means in a body of a human.
(8) A therapeutic agent of kidney cancer, which comprises, as an active ingredient, a compound of the formula (I)

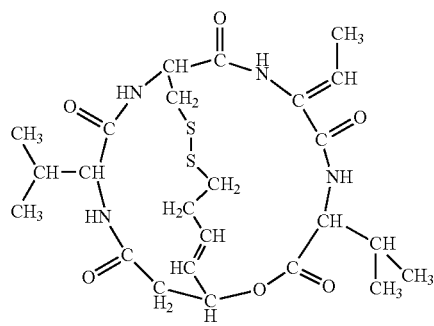
(I)

or a salt thereof.

(9) The therapeutic agent according to the above-mentioned (8), wherein the compound of the formula (I) is a compound of the formula (II)

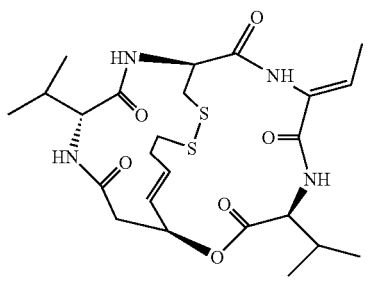
(II)

(10) The therapeutic agent according to the above-mentioned (8), which has an antitumor activity in vivo.
(11) The therapeutic agent according to the above-mentioned (8), which is used for a human.
(12) Use of a compound of the formula (I)

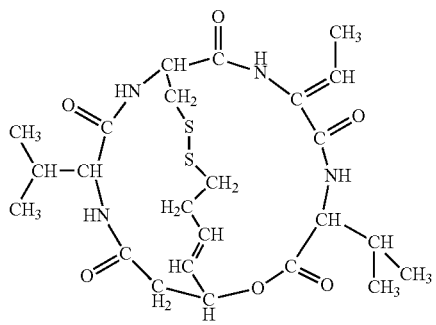
(I)

or a salt thereof, for the production of a therapeutic agent of kidney cancer.

(13) The use according to the above-mentioned (12), wherein the compound of the formula (I) is a compound of the formula (II)

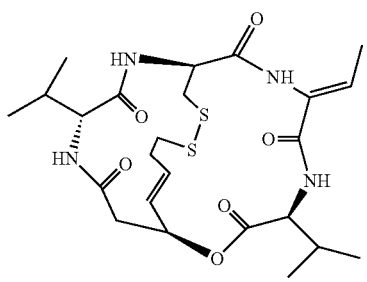
(II)

(14) The use according to the above-mentioned (12), wherein the above-mentioned therapeutic agent of kidney cancer has an antitumor activity in vivo.
(15) The use according to the above-mentioned (12), wherein the above-mentioned therapeutic agent of kidney cancer is used for a human.
(16) A pharmaceutical composition for treating kidney cancer, which comprises a compound of the formula (I)

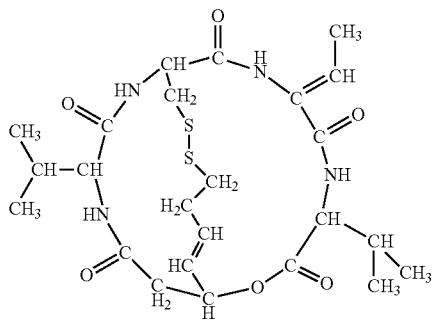

(I)

or a salt thereof, and a pharmaceutically acceptable carrier.
(17) The pharmaceutical composition of the above-mentioned (16), wherein the compound of the formula (I) is a compound of the formula (II)

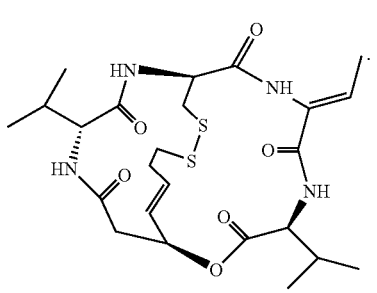

(II)

(18) The pharmaceutical composition of the above-mentioned (16), which has an antitumor activity in vivo.
(19) The pharmaceutical composition of the above-mentioned (16), which is used for a human.
(20) A commercial package comprising a pharmaceutical composition of any of the above-mentioned (16) to (19) and a written matter associated therewith, the written matter stating that the pharmaceutical composition can or should be used for treating kidney cancer.

BRIEF DESCRIPTION OF THE DRAWING

FIG. 1 is a graph showing the antitumor activity of FR901228 against human kidney tumor (RXF-631L) transplanted in mouse.

DETAILED DESCRIPTION OF THE INVENTION

The therapeutic agent of kidney cancer of the present invention contains, as an active ingredient, a compound of the formula (I) (hereinafter to be also referred to as FK228) or a salt thereof. The treatment method of kidney cancer of the present invention includes administering an effective amount of FK228 to mammals inclusive of human. Of the compounds of the formula (I), preferred is a compound of the formula (II), which is a stereoisomer (hereinafter to be also referred to as FR901228). These compounds have a potent histone deacetylase inhibitory activity (Nakajima, H. et al.; ibid (1998)), and particularly FR901228 has an even more potent histone deacetylase inhibitory activity. Therefore, it is suitably included in the therapeutic agent of kidney cancer of the present invention, and can be suitably used for the treatment method of kidney cancer of the present invention.

Unless otherwise specified, a simple reference to FK228 in the present specification means a group of compounds, irrespective of the stereoisomerism, including a compound of the formula (II).

FK228 and a salt thereof are known substances and are obtainable. For example, FR901228, which is one of the stereoisomers of FK228, can be obtained by culturing, under aerobic conditions, a bacterial strain belonging to the genus *Cromobacterium*, which is capable of producing FR901228, and recovering the substance from the culture broth. The bacterial strain belonging to the genus *Cromobacterium*, which is capable of producing FR901228, is exemplified by *Cromobacterium violaceum* WB968 (FERM BP-1968). An FR901228 substance can be obtained from this production cell according to the disclosure of JP-B-7-64872. It is preferable to obtain FR901228 from a bacterial strain belonging to the genus *Cromobacterium*, which is capable of producing FR901228, because FR901228 can be obtained more easily. However, synthetic or semi-synthetic FR901228 is also advantageous because an additional purification step is not necessary or can be made simple. Similarly, FK228 other than FR901228 can be synthesized or semi-synthesized by a method conventionally known. To be specific, it can be produced according to the method reported by Khan W. Li, et al. (J. Am. Chem. Soc., vol. 118, 7237-7238 (1996)).

The salt of FK228 is a biologically acceptable salt, which is generally non-toxic, and is exemplified by salts with base or acid addition salts, inclusive of salts with inorganic base such as alkali metal salt (e.g., sodium salt, potassium salt etc.), alkaline earth metal salt (e.g., calcium salt, magnesium salt etc.), ammonium salt, salts with organic base such as organic amine salt (e.g., triethylamine salt, diisopropylethylamine salt, pyridine salt, picoline salt, ethanolamine salt, triethanolamine salt, dicyclohexylamine salt, N,N'-dibenzylethylenediamine salt etc.), inorganic acid addition salt (e.g., hydrochloride, hydrobromide, sulfate, phosphate etc.), organic carboxylic•sulfonic acid addition salt (e.g., formate, acetate, trifluoroacetate, maleate, tartrate, fumarate, methanesulfonate, benzenesulfonate, toluenesulfonate etc.), salt with basic or acidic amino acid (e.g., arginine, aspartic acid, glutamic acid etc.), and the like.

FK228 has stereoisomers based on asymmetric carbon atom and double bond, such as optical isomer, geometric isomer and the like, all of which and mixtures thereof are also encompassed in the present invention.

Further, solvate compounds (e.g., inclusion compound such as hydrate etc.) of FK228, FR901228 and salts thereof are also encompassed in the present invention.

In the present invention, in vivo and in vitro means as these terms are used in this field. That is, "in vivo" means that the target biological functions and responses are expressed in the body, such as in the body of various mammals to be mentioned below, preferably in the body of a human. The term "in vitro" means that such functions and responses are expressed in test tubes including tissue culture system, cell culture system, cell free system and the like.

FK228, which is a histone deacetylase inhibitor, exerts an antitumor activity against various tumors. Among others, it shows a noticeable effect in vivo and in human against kidney cancer.

The therapeutic agent of kidney cancer of the present invention can be used for mammals such as human, dog, bovine, horse, rat, guinea pig and the like.

The therapeutic agent of kidney cancer of the present invention can be used in the form of a solid, semi-solid or liquid pharmaceutical preparation containing FK228 or a salt thereof as an active ingredient in admixture with an organic or inorganic carrier or excipient suitable for oral or parenteral application. The active ingredient can be admixed with a typical, non-toxic pharmaceutically acceptable carrier suitable for the dosage form, such as powder, tablet, pellet, capsule, suppository, liquid, emulsion, suspension, aerosol, spray and other form for use. Where necessary, auxiliary agent, stabilizer, tackifier and the like may be used. These carriers and excipients may be sterilized where necessary, or a sterilization treatment may be applied after formulation into a preparation. FK228 and a salt thereof are contained in the therapeutic agent of kidney cancer in an amount sufficient to produce a therapeutic effect on kidney cancer, such as suppression of infiltration into surrounding tissues, metastasis to a distal part, and growth of cancer.

The method of administering the therapeutic agent of kidney cancer of the present invention is free of any particular limitation as long as it can provide a therapeutic effect on kidney cancer described above. Particularly when the therapeutic agent of kidney cancer of the present invention is used, parenteral administration is preferable, namely, intravenous administration, intramuscular administration, direct administration into the tissue, administration into nostril cavity, intradermal administration, administration into cerebrospinal fluid, administration into biliary tract, intravaginal administration and the like. In addition, a liposome method and the like can be preferably used. When this therapeutic agent is applied to a human, intravenous administration, intramuscular administration or oral administration is preferably employed for the application. A therapeutically effective amount of the active ingredient, FK228 or a salt thereof, varies depending on the age and condition of individual patients to be treated, and the type of cancer. In the case of intravenous administration, the daily dose of FK228 is generally 0.1-100 mg, preferably 1-50 mg, more preferably 5-30 mg, per $m^2$ of the body surface area of human, which is continuously administered by infusion to treat the tumor. The time of continuous administration by infusion varies depending on the dose. It is preferably 3-6 h, more preferably 3.5-4.5 h, most preferably 4 h. The administration frequency is based on a cycle containing 1 to 4 times of administration(s) at 18-30 day intervals, and 2 to 7 such cycles are preferably applied. Additionally, the combination treatment with FK228 and retinoic acid (preferably all-trans-retinoic acid: ATRA) is also preferable.

The present invention is described in more detail in the following by way of Examples. The present invention is not limited in any way by these Examples.

EXAMPLE 1

Antitumor Effect of FK228 on Human Renal Tumor Xenograft (1) Preparation of Drug A recommended amount of FR901228 was weighed, a solvent (10% HCO-60 (Nihon Surfactant Kogyo K.K./saline) was added and the mixture was ultrasonicated for dissolution. The positive control substance, Taxol, was dissolved in Cremophor EL (SIGMA/ethanol (1:1)) to a concentration of 24 mg/mL before test and preserved in refrigerator. When in use, a 9-fold amount of physiological saline was added to dilute the substance to 2.4 mg/mL (solvent component: 5% Cremophor EL-5% ethanol-90% saline).

(2) Animals

For the antitumor activity test of the drug, BALB/cANnNCrj-nu/nu mice (female, 6-week-old) were purchased from Charles River Japan (Yokohama, Japan), and after acclimation for more than 1 week, subjected to the test. The mice were reared in an SPF environment, where free access to water and feed was allowed.

(3) Tumor $2\text{-}3\times10^7$ Human renal tumor (RXF-631L: Cancer Chemotherapy Center, Japan Foundation for Cancer Research, Tokyo, Japan) was maintained subcutaneously by serial passage in BALB/cANnNCrj-nu/nu mice.

(4) Experimental Implantation and Grouping

Fragments (3×3×3 mm) of RXF-631L tumor were subcutaneously implanted into the right flank of BALB/cANnNCrj-nu/nu mice. When the tumor volume reached 100-300 $mm^3$ after the tumor implantation, the mice were grouped (6 per group) avoiding dispersion in the tumor volume. The tumor volume was calculated from the formula: tumor volume $(mm^3)=\frac{1}{2}\times L\times W^2$ where L and W represent the length and width of the tumor mass, respectively.

(5) Administration

The administration was started on the day the mice were grouped (Day 0). FR901228 (3.2 and 1.8 mg/kg) was intravenously administered to the FR901228 administration group 3 times every 4 days (q4d×3). The positive control substance, Taxol, was intravenously administered (24 mg/kg) to the Taxol administration group for 5 consecutive days (qd×5). The solvent alone (10% HCO-60/saline) was administered to the control group (q4d×3). The liquid amount of administration was calculated based on the body weight measured on the day of administration (0.1 mL/10 g body weight). The MTD (maximum tolerance dose) of FR901228 and Taxol was 3.2 mg/kg/day (q4d×3) and 24 mg/kg/day (qd×5), respectively.

(6) Measurement of Tumor Size and Body Weight

The tumor size (length, width) and body weight were measured twice a week from Day 0.

The results are shown in FIG. 1, wherein -●- shows a shift in the size of tumor in the control group, -■- shows that by the administration of 1.8 mg/kg of FR901228, -▲- shows that by the administration of 3.2 mg/kg of FR901228 and -♦- shows that by the administration of 24 mg/kg of Taxol. FR901228 suppressed the growth of human kidney cancer in vivo.

EXAMPLE 2

Antineoplastic Response

One patient (Patient Number 31-00-83-2) demonstrated a partial response. This patient was a 38-years-old female with a history of clear cell renal carcinoma that was diagnosed in 1996. The patient received a total of 10 doses of FR901228: FR901228 was administered at 9.10 $mg/m^2$ on day 1 and day 5 of the first cycle (21 days), 9.10 $mg/m^2$ on day 1 of the second cycle (21 days), 9.10 $mg/m^2$ on day 1 and day 5 of the third cycle (28 days), 9.10 $mg/m^2$ on day 1 of the fourth cycle (22 days), 12.70 $mg/m^2$ on day 1 of the fifth cycle (20 days), 17.8 $mg/m^2$ on day 1 of the sixth cycle (23 days), 17.8 $mg/m^2$ on day 1 of the seventh cycle (23 days) and 17.8 $mg/m^2$ on day 1 of the eighth cycle (21 days) by continuous infusion for 4 hours. The treatment effect was evaluated based on the RECIST criteria. This patient experienced a partial response after the first two cycles and disease progression was noted after cycle 8.

INDUSTRIAL APPLICABILITY

The therapeutic agent of kidney cancer of the present invention comprising FK228 (particularly FR901228) or a salt thereof, having a histone deacetylase inhibitory activity, as an active ingredient shows a superior antitumor activity not only in vitro but also in vivo. The therapeutic agent of kidney cancer of the present invention shows a superior antitumor activity in human patients with kidney cancer. Therefore, the present invention can be suitably applied for the treatment of kidney cancer.

Free-Text of Sequence Listing

SEQ ID NO: 1: Xaa is an amino acid represented by the formula $NH_2C(CHCH_3)COOH$. In the formula $COOHCH_2CH(CHCHC_2H_4SH)OH$, the carboxylic group is bonded with the amino group of the first amino acid Val, the hydroxyl group is bonded with the carboxylic group of the fourth amino acid Val, and the SH group is bonded with the SH group of the second amino acid Cys via a disulfide bond.

This application is based on a patent application No. 60/369,868 filed in U.S., the contents of which are hereby incorporated by reference.

SEQUENCE LISTING

```
<160> NUMBER OF SEQ ID NOS: 1

<210> SEQ ID NO 1
<211> LENGTH: 4
<212> TYPE: PRT
<213> ORGANISM: Chromobacterium sp.
<220> FEATURE:
<221> NAME/KEY: SITE
<222> LOCATION: (1)..(2)
<223> OTHER INFORMATION: In the formula COOHCH2CH(CHCHC2H4SH)OH, the
      COOH group is COOH group of the fourth amino acid Val, and the SH
      group is bonded with the SH group of the second amino acid Cys via
      a disulfide bond.
<220> FEATURE:
<221> NAME/KEY: MISC_FEATURE
<222> LOCATION: (3)..(3)
<223> OTHER INFORMATION: Xaa is an amino acid represented by the formula
      NH2C(CHCH3)COOH.
<220> FEATURE:
<221> NAME/KEY: SITE
<222> LOCATION: (4)..(4)
<223> OTHER INFORMATION: In the formula COOHCH2CH(CHCHC2H4SH)OH, the
      COOH group is COOH group of the fourth amino acid Val, and the SH
      group is bonded with the SH group of the second amino acid Cys via
      a disulfide bond.

<400> SEQUENCE: 1

Val Cys Xaa Val
1
```

The invention claimed is:

1. A method of treating kidney cancer in a mammal in need thereof, which comprises administering an effective amount of a compound of the formula (I)

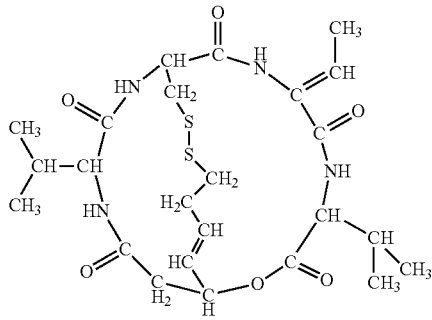

(I)

or a salt thereof to said mammal.

2. The treatment method of kidney cancer according to claim 1, wherein the compound of the formula (I) is a compound of the formula (II)

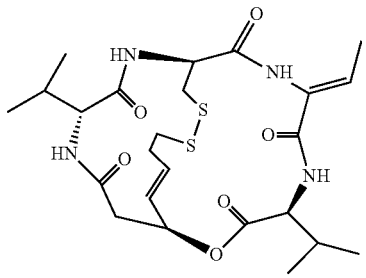

(II)

3. The treatment method of kidney cancer according to claim 1, wherein the mammal is a human.

4. A method of suppressing growth of a cancerous tumor of the kidney in vivo in a mammal in need thereof, which comprises administering an effective amount of a compound of the formula (I)

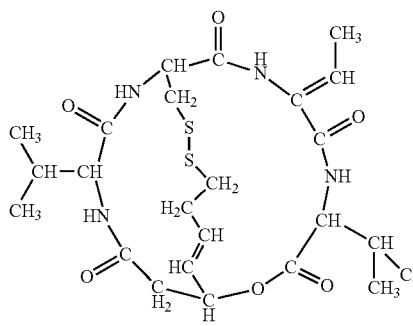

(I)

or a salt thereof to said mammal.

5. The method of suppressing growth of the cancerous tumor of the kidney according to claim 4, wherein the compound of the formula (I) is a compound of the formula (II)

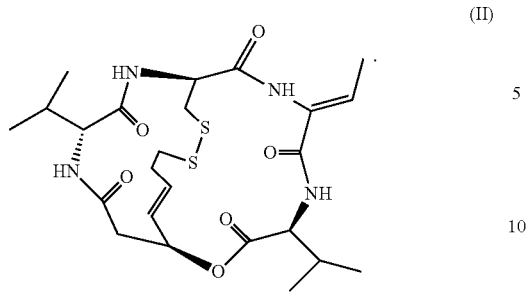
(II)
6. The method of claim 4, wherein the in vivo means in a body of a human.